(12) United States Patent
Noike et al.

(10) Patent No.: US 6,860,996 B2
(45) Date of Patent: Mar. 1, 2005

(54) METHOD OF PRODUCING HYDROGEN GAS BY USING HYDROGEN BACTERIA

(75) Inventors: Tatsuya Noike, Sendai (JP); Osamu Mizuno, Nara (JP); Takashi Miyahara, Hamamatsu (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 10/250,523

(22) PCT Filed: Dec. 19, 2001

(86) PCT No.: PCT/JP01/11167

§ 371 (c)(1),
(2), (4) Date: Jun. 30, 2003

(87) PCT Pub. No.: WO03/052112

PCT Pub. Date: Jun. 26, 2003

(65) Prior Publication Data

US 2004/0050778 A1 Mar. 18, 2004

(51) Int. Cl.[7] .............................. C02F 3/32; C02F 3/34
(52) U.S. Cl. ...................... 210/603; 210/612; 210/631
(58) Field of Search ................................ 210/603, 612, 210/631, 175, 205; 423/644, 650

(56) References Cited

U.S. PATENT DOCUMENTS

| | | | |
|---|---|---|---|
| 3,711,392 A | * 1/1973 | Metzger | 210/603 |
| 4,354,936 A | * 10/1982 | Ishida et al. | 210/602 |
| 5,464,539 A | * 11/1995 | Ueno et al. | 210/603 |
| 5,525,229 A | * 6/1996 | Shih | 210/603 |
| 5,648,258 A | 7/1997 | Odom | 435/252.1 |
| 6,299,774 B1 | * 10/2001 | Ainsworth et al. | 210/603 |
| 6,569,332 B2 | * 5/2003 | Ainsworth et al. | 210/603 |

FOREIGN PATENT DOCUMENTS

| | | |
|---|---|---|
| JP | 5-096294 | 4/1993 |
| JP | 7-031484 | 2/1995 |
| JP | 7-031998 | 2/1995 |
| JP | 8-308591 | 11/1996 |

OTHER PUBLICATIONS

Steven W. Van Ginkel et al., Biohydrogen Production Potential Using Variable Natural Inocula, Annual Conference & Exposition on Water Quality and Wastewater Treatment, 2000, p. 3413–3429.

* cited by examiner

*Primary Examiner*—Fred G. Prince
(74) *Attorney, Agent, or Firm*—Gary C Cohn PLLC

(57) ABSTRACT

Both organic waste or wastewater and methane-generating bacteria are contained in organic waste or wastewater. When organic waste or wastewater containing these bacteria is cultured as a base material, the hydrogen produced by the hydrogen-generating bacteria is consumed by the methane-generating bacteria. The purpose of the invention is achieved by controlling the biophase with heat treatment so that the activity of hydrogen-generating bacteria having sporulation ability contained in the organic waste is maintained, while the hydrogen-consuming, methane-producing bacteria are decreased. Specifically, this invention provides a method of effectively generating hydrogen gas using hydrogen-generating bacteria by adjusting the treatment temperature to 68–95° C., and adjusting the treatment time and pH.

20 Claims, No Drawings

METHOD OF PRODUCING HYDROGEN GAS BY USING HYDROGEN BACTERIA

FIELD OF THE INVENTION

This invention relates to a method of generating hydrogen gas efficiently using hydrogen-generating bacteria, by heat-treating organic waste under specific conditions.

PRIOR ART

Various types of germs are contained in organic waste or wastewater. The various germs mixed in processes which treat organic waste and wastewater contain both useful microorganisms and microorganisms which have a negative effect. For this reason, in the prior art, refractory organic substances were solubilized by carrying out high temperature treatment of organic waste or wastewater at 130–180° C. (Li Yu You, Tatsuya Noike (1989), "The effect of pre-heat treatment and residence time on the anaerobic digestion of excess sludge", Water Pollution Research, 12(2), 112–121"), but due to the high temperature used, useful microorganisms were also sterilized, and energy consumption was high.

Of the anaerobic bacteria contained in these germs, there are some in the genus *Clostridium* which have hydrogen-generating ability, and when they are independently cultured, hydrogen is actively generated. However, since anaerobic hydrogen-consuming methane-generating bacteria are also present in nature, when organic waste such as raw sludge or kitchen garbage containing these bacteria is cultured as a substrate, the generated hydrogen is consumed and is promptly converted into methane, so the apparent yield of hydrogen gas falls. Therefore, in hydrogen production using an anaerobic non-photosynthetic bacterium, it is essential to find a means of reducing hydrogen-consuming bacteria, such as hydrogen-consuming, methane-generating bacteria. It has been reported in the literature that an inhibitor such as chloroform can be added to inactivate hydrogen-consuming, methane-generating bacteria and thereby increase hydrogen-generating ability, but it is known that in general, this inhibitory effect declines during long periods of operation, and a toxic inhibitor remains in the waste after hydrogen generation. Hence, an effective method had not been found.

Problems which this Invention Attempts to Solve

In order to eliminate microorganisms which have a negative effect, such as hydrogen-consuming, methane-generating bacteria contained in organic waste or wastewater, it is usual to autoclave at 121° C. for 20 minutes on a laboratory scale, but this technique is not effective in actual processes. It is therefore an object of this invention to provide a means, by heat-treating under controlled conditions, of reducing only the hydrogen consumption activity of bacteria, such as hydrogen-consuming, methane-generating bacteria, contained in organic waste or wastewater, and thus of making effective use of anaerobic non-photosynthesizing hydrogen-generating bacteria.

Means for Solving the above Problems

Most microorganisms have temperature specificity, and most microorganisms inactivate at about 60–90° C. However, microorganisms having sporulation ability are highly heat resistant, and this method is therefore considered particularly effective when microorganisms having sporulation ability are specifically selected.

The inventors noted that some anaerobic non-photosynthetic bacteria which generate hydrogen are microorganisms having such sporulation ability, and have a high heat resistance. They also succeeded in discovering conditions for specifically selecting only hydrogen-generating bacteria.

This invention achieves control of the biota by heat treatment aimed at reducing hydrogen-consuming, methane-generating bacteria while maintaining the activity of hydrogen-generating bacteria having sporulation ability contained in organic waste.

Thus, by efficiently employing only the hydrogen-generating bacteria, useful hydrogen gas, which is an energy source and is also a raw material for chemical plants, can be produced using organic waste as a raw material.

This invention provides a method of effectively using hydrogen-generating bacteria by adopting a treatment temperature of 68–95° C., and by adjusting treatment time and pH.

As hydrogen-consuming, methane-generating bacteria are destroyed by higher treatment temperatures, a higher temperature is preferred, but as the destruction of hydrogen-generating bacteria simultaneously increases, 68–95° C. is suitable for the treatment temperature range. Also, hydrogen-consuming, methane-generating bacteria are destroyed at lower pH, so a lower pH is preferred, but as the destruction of hydrogen-generating bacteria simultaneously increases, the minimum pH is about 3.7. Treatment time is described later, but energy consumption increases with longer treatment times, which is undesirable, so an upper limit is set from this viewpoint.

The present invention is therefore a method of generating hydrogen gas using hydrogen-generating bacteria comprising a step of treating organic waste or wastewater under anaerobic conditions, and adjusting pH and treatment temperature to correspond to any of the conditions A–F of Table 1. It is also a method of generating hydrogen gas wherein the treatment time in A–C of Table 1 is at least 10 minutes, and the treatment time in D–F of Table 1 is at least 60 minutes.

TABLE 1

| | | pH | | |
|---|---|---|---|---|
| | | 3.7 to 5.7 | more than 5.7 to 8.0 | more than 8.0 to 9.0 |
| Treatment Temperature (° C.) | 68 to less than 75 | A | — | — |
| | 75 to less than 85 | B | D | — |
| | 85 to less than 95 | C | E | F |

In this Table 1, the treatment times in A–C are respectively, preferably at least 30 minutes, but more preferably 60 minutes. The treatment times in D–F are respectively, preferably at least 90 minutes, but more preferably at least 120 minutes.

By treating organic waste and wastewater under anaerobic conditions which combine this treatment temperature, treatment time and pH, it is possible to inactive hydrogen-consuming methane-generating bacteria, to activate hydrogen-generating bacteria, and to generate hydrogen gas to the maximum extent.

DETAILED DESCRIPTION OF THE INVENTION

Examples of the organic waste and wastewater which can be used in the method of this invention are organic waste and wastewater from factories such as food processing plants, bioculture plants, petroleum plants, chemical plants and pharmaceutical plants, total waste and wastewater containing organic waste such as agricultural waste, feces and urine, raw sludge and slot sludge, and sludge at the bottom of lakes and marshes. Waste and wastewater from food processing plants or bioculture plants, or agricultural waste, feces and urine, raw sludge, sludge at the bottom of lakes and marshes or slot sludge, are particularly suitable. Hydrogen-forming bacteria and methane-generating bacteria are bacteria present in the natural environment, and it is thought that they also inhabit this organic waste.

The hydrogen-generating bacteria which have activity in this invention are preferably those of the *Clostridium* group. Examples of *Clostridium* group bacteria are those listed in the following Table 2 (M. Ingram: "In the Bacterial Spore (G. W. Gould, A. Hurst ed.), p577, Academic Press, London). The value D in the table represents the time for which they can withstand this temperature. It is seen that the spores of most *Clostridium* group bacteria can withstand a value D of at least 80° C.

TABLE 2

| Name of sporulating bacterium | D value (min) | | |
| --- | --- | --- | --- |
| | 120° C. | 100° C. | 80° C. |
| Cl. thermosaccharolyticum | 3~4 | | |
| Cl. nigrificans | 2~3 | | |
| Cl. sporogenes | 0.1~1.5 | | |
| Cl. botulinum A and B | 0.1~0.2 | 50 | |
| Cl. perfringens | | 0.3~20 | |
| Cl. caloritolerans | | 3 | |
| Cl. hisolyticum | | 1 | 115 |
| Cl. butyricum | | | |
| Cl. pasteurianum | | 0.1~0.5 | |
| Cl. sordellii | | | 40 |
| Cl. subterminale | | | 30 |
| Cl. botulinum E | | | 0.3~3 |

There are also some types of *Clostridium* bacteria which have pathological activity, such as *Cl.botulinum, Cl.hystolyticum* and *Cl.perfringens*, and are therefore unsuitable. *Clostridium* group bacteria appropriate for use in the present invention include *Cl.thermosaccharolyticum, Cl.butyricum* and *Cl.pasteurianum*.

It is thought that except for some sporulation bacteria, high temperature bacteria and medium temperature bacteria of the *Clostridium* group, the bacteria lose their activity at about 60–90° C.

Hereafter, this invention will be described by means of some examples, but these are not meant to limit this invention in any way.

EXAMPLES

A sludge obtained by storing an anaerobic digestion sludge extracted from an anaerobic digestion tub of raw sludge at room temperature for about three months, was used as a sample for heat treatment.

20 mL of this heat treatment sample was introduced into a vial, the initial pH was adjusted from 4.0 to 10.0, and the sample was then treated using a water bath at 60, 70, 80 and 90° C. respectively for 10 or 60 minutes. Herein, the pH was adjusted by adding a suitable amount of 1N HCl solution or 1N NaOH solution to the vial into which 20 mL of the heat treatment sample had been introduced. Regarding the amount of 1N HCl solution or 1N NaOH solution, this was taken as the amount which gave the desired pH when 1N HCl solution or 1N NaOH solution was added to a vial provided with a pH sensor containing an identical sample. The heat treatment time was taken as the elapsed time after the heat treatment sample reached a set temperature.

After heat treatment, the effect of surplus heat was suppressed by quenching in ice water. The pH of the sample after heat treatment was adjusted to 7.0, and 60 mL of a sterilized medium having glucose as carbon source was added. The medium shown in Table 3 was used as a culture medium after autoclave sterilization (121° C., 20 minutes). Then, the culture medium was cultured at 35° C. for four weeks.

TABLE 3

| Glucose | 3.0 g/L |
| --- | --- |
| Yeast extract | 0.5 g/L |
| $KH_2PO_4$ | 0.4 g/L |
| $K_2HPO_4$ | 0.4 g/L |
| $NH_4Cl$ | 1.0 g/L |
| $MgCl_2.6H_2O$ | 0.1 g/L |
| Mineral solution [1] | 10 mL/L |
| Vitamin solution [2] | 10 mL/L |
| $NaHCO_3$ | 6.0 g/L |
| L-cysteine.HCl—$H_2O$ | 0.5 g/L |
| $Na_2S.9H_2O$ | 0.25 g/L |
| Resazurin | 0.002 g/L |

The substances in Table 4 and Table 5 were used, respectively, as the mineral solution [1] and the vitamin solution [2] in Table 3.

TABLE 4

(Mineral solution)

| $N(CH_2COOH)_3$ | 4.5 g/L |
| --- | --- |
| $FeCl_2.4H_2O$ | 0.40 g/L |
| $CoCl_2.6H_2O$ | 0.12 g/L |
| $AlK(SO_4)_2$ | 0.01 g/L |
| NaCl | 1.00 g/L |
| $CaCl_2$ | 0.02 g/L |
| $Na_2MoO_4$ | 0.01 g/L |
| $MnCl_2.4H_2O$ | 0.1 g/L |
| $ZnCl_2$ | 0.1 g/L |
| $H_3BO_3$ | 0.01 g/L |
| $CuSO_4.H_2O$ | 0.01 g/L |
| $NiCl_2.6H_2O$ | 0.02 g/L |

TABLE 5

(Vitamin solution)

| Biotin | 2 mg/L |
| --- | --- |
| Folic acid | 2 mg/L |
| Pyridoxine hydrochloride | 10 mg/L |
| Thiamine hydrochloride | 5 mg/L |
| Riboflavin | 5 mg/L |
| Nicotinic acid | 5 mg/L |
| DL-calcium pantothenate | 5 mg/L |
| Vitamin B12 | 0.1 mg/L |
| p-aminobenzoic acid | 5 mg/L |
| Lipoic acid | 5 mg/L |

All operations, such as preparation of culture media, dilution and inoculation were performed under anaerobic conditions. For anaerobic operations, the Hungate gas injection method was used, and the injection gas was 80% $N_2$+20% $CO_2$ mixed gas deoxidized at 330° C. by a reduced copper column. The composition of the dilution water is shown in Table 6.

TABLE 6

| | |
|---|---|
| $KH_2PO_4$ | 0.4 g/L |
| $K_2HPO_4$ | 0.4 g/L |
| $NH_4Cl$ | 1.0 g/L |
| $MgCl_2.6H_2O$ | 0.1 g/L |
| $NaHCO_3$ | 4.36 g/L |
| 0.1% resazurin | 2.0 mL/L |
| L-cysteine.HCl—$H_2O$ | 0.5 g/L |
| $Na_2S.9H_2O$ | 0.25 g/L |

The culture media used for counting bacterial groups are shown in Table 7.

TABLE 7

| Composition | Hydrogen-consuming methane-generating bacillus | Hydrogen-generating bacillus |
|---|---|---|
| Glucose | — | 3.0 g/L |
| Vapor phase part gas | 80% $H_2$ + 20% $CO_2$ | 80% $N_2$ + 20% $CO_2$ |
| Yeast extract | 0.2 g/L | 0.2 g/L |
| $KH_2PO_4$ | 4.0 g/L | 4.0 g/L |
| $K_2HPO_4$ | 4.0 g/L | 4.0 g/L |
| $NH_4Cl$ | 10.0 g/L | 10.0 g/L |
| $MgCl_2.6H_2O$ | 1.0 g/L | 1.0 g/L |
| Mineral solution[1] | 10 mL/L | 10 mL/L |
| Vitamin solution[2] | 10 mL/L | 10 mL/L |
| $NaHCO_3$ | 6.0 g/L | 6.0 g/L |
| L-cysteine.HCl—$H_2O$ | 0.5 g/L | 0.5 g/L |
| $Na_2S.9H_2O$ | 0.2 g/L | 0.2 g/L |
| Resazurin | 0.002 g/L | 0.002 g/L |

*The mineral solution[1] and the vitamin solution[2] are identical to those of Table 3.

The dilution water and the medium were sterilized by high pressure steam at 120° C. using an autoclave. However, in the case of hydrogen-consuming, methane-generating bacteria, the vapor phase part after sterilization was pressurized to 1.5 atmospheres by 80% $H_2$+20% $CO_2$ gas which had passed through a 0.22 μm membrane filter.

The chemical composition (proportion of hydrogen and methane) and generation amount of the biogas produced from the vapor phase part of the vial, were measured at effectively fixed intervals over the whole culture period. The number of moles of hydrogen and methane generated at each period were measured from the data for each period, and the ratio of the total number of moles of hydrogen (methane) obtained by summing over the whole experimental period (four weeks) to the number of moles of glucose added to the vial when the experiment started, was taken as the hydrogen yield (methane yield).

The MPN method was used for measurement of bacterial count. Specifically, a vial containing 90 mL of the dilution water was inoculated with 10 mL of sample (this solution was a 10 strength sample), and a 10 n strength sample was prepared by repeating the same operation. Next, samples diluted to different strengths were injected in 1 mL aliquot parts by a sterilized disposable syringe into a test-tube containing the medium for bacterial counts. Herein, three test-tubes were inoculated with a sample of each dilution strength. The inoculated test-tubes were cultured at 36±1° C. for four weeks in the case of methane-generating bacteria, and for three days in the case of hydrogen-generating bacteria. After culture, the gas composition of the vapor phase part of the test tube was measured. Test-tubes were taken as positive if they were found to contain methane or hydrogen, and negative if they did not. The gas composition was measured using gas chromatography. The number of positive test-tubes of the samples of each dilution strength, the hydrogen-generating bacterial count and the methane-generating bacterial count were found using the MPN Code Table (Method 3-3-3) for sewage testing.

Table 8 shows the hydrogen and methane yield after 28 days for untreated sludge, and for heat-treated samples of different pH.

TABLE 8

| Heat treatment temperature (° C.) | Time (min) | Yield of methane moles ($CH_4$)/moles (glucose) pH | | | Yield of hydrogen moles ($H_2$)/moles (glucose) pH | | |
|---|---|---|---|---|---|---|---|
| | | 5.5 | 7.4 | 8.5 | 5.5 | 7.4 | 8.5 |
| 60 | 10 | 2.63 | 3.13 | 3.29 | 0.97 | 0.47 | 0.99 |
| | 60 | 0.06 | 3.20 | 1.67 | 0.99 | 0.86 | 1.24 |
| 70 | 10 | 0.00 | 0.47 | 0.58 | 1.42 | 1.13 | 1.39 |
| | 60 | 0.00 | 0.43 | 0.00 | 1.55 | 1.24 | 1.39 |
| 80 | 10 | 0.00 | 0.27 | 3.07 | 1.52 | 1.37 | 1.50 |
| | 60 | 0.00 | 0.11 | 2.33 | 1.51 | 1.28 | 1.44 |
| 90 | 10 | 0.00 | 0.22 | 0.55 | 1.38 | 1.06 | 1.05 |
| | 60 | 0.00 | 0.00 | 0.00 | 1.20 | 0.78 | 1.05 |
| Untreated | — | — | 3.60 | 0 | 0 | 0.37 | — |

At pH 5.5, although the hydrogen yield was high at 70 and 80° C., it fell at 90° C. Methane was not generated at all by heat treatment at 70° C. or more. At pH 7.4, the hydrogen yield was high when the heat treatment temperature was 70 and 80° C., and methane generation was also observed except for the case of heat-treatment at 90° C. for 60 minutes. At pH 8.5, the hydrogen yield was a maximum at 80° C. Methane generation was observed at all heat treatment temperatures.

Table 9 shows bacterial counts of hydrogen-generating bacteria and hydrogen-consuming methane-generating bacteria in a sample heat-treated at pH 5.5, 7.4 and 8.5 at 60, 70, 80 and 90° C. for 60 minutes. A sample before heat treatment is also shown (shown as "initial stage" in the table).

TABLE 9

| Heat treatment temperature (° C.) | Number of hydrogen-generating bacteria pH | | | Number of hydrogen-consuming methane generating bacteria pH | | |
|---|---|---|---|---|---|---|
| | 5.5 | 7.4 | 8.5 | 5.5 | 7.4 | 8.5 |
| Initial stage | 4.3 × $10^4$ | 4.3 × $10^4$ | 4.3 × $10^4$ | 2.4 × $10^5$ | 2.4 × $10^5$ | 2.4 × $10^5$ |
| 60 | 4.3 × $10^4$ | 4.3 × $10^4$ | 2.4 × $10^5$ | 2.4 × $10^4$ | 2.4 × $10^4$ | 2.4 × $10^4$ |
| 70 | 9.3 × $10^4$ | 9.3 × $10^4$ | 7.5 × $10^4$ | 3.6 × 10 | 2.3 × $10^2$ | 2.4 × $10^3$ |
| 80 | 4.3 × $10^4$ | 4.3 × $10^3$ | 4.3 × $10^3$ | 0 | 0 | 0 |
| 90 | 9.3 × $10^2$ | 1.5 × $10^2$ | 4.3 × $10^2$ | 0 | 0 | 0 |

At pH 5.5, when the heat treatment temperature was 80° C. or less, the hydrogen-generating bacterial count was almost constant, but at 90° C., it decreased to 1/100. At pH 7.4, and 60 and 70° C., a large difference in the hydrogen-generating bacterial count was not observed, but at 80° C., it fell to about 1/20, and at 90° C., to about 1 in 600. At pH 8.5, as the heat treatment temperature increased to 60, 70, 80 and 90° C., the hydrogen-generating bacterial count gradually decreased. When the heat treatment temperature reached 70° C., the decrease rate of the hydrogen-consuming, methane-generating bacterial count became larger as the pH fell. At any pH, at a heat treatment temperature of 80° C. or more, the hydrogen-consuming, methane-generating bacteria died or remarkably decreased. The result that hydrogen-consuming, methane-generating bacteria have more heat resistance under alkaline conditions than under acid conditions, is in agreement with the result that the methane yield falls when the pH during heat treatment shown in Table 1, is low.

The above shows that, by performing heat-treatment under anaerobic conditions combining the treatment temperature, treatment time and pH according to this invention, microflora can be controlled to be suitable for hydrogen-generating.

What is claimed is:

1. A method of generating hydrogen gas using a hydrogen-generating bacteria comprising a heat-treating step of treating organic waste or wastewater under anaerobic conditions at any of the pH and treatment temperatures of A–F of Table 1, wherein the treatment time is at least 10 minutes in A–C of Table 1, and the treatment time is at least 60 minutes in D–F of Table 1, wherein hydrogen-consuming, methane-producing bacteria contained in the organic waste or wastewater are selectively inactivated during the heat-treating step, and then culturing the treated organic waste or wastewater to generate hydrogen gas.

TABLE 1

| | | pH | | |
|---|---|---|---|---|
| | | 3.7 to 5.7 | more than 5.7 to 8.0 | more than 8.0 to 9.0 |
| Treatment Temperature (° C.) | 68 to less than 75 | A | — | — |
| | 75 to less than 85 | B | D | — |
| | 85 to less than 95. | C | E | F |

2. The method according to claim 1, wherein, in Table 1, the treatment time is at least 30 minutes in at least one of A–C, and the treatment time is at least 90 minutes in at least one of D–F.

3. The method according to claim 2, wherein said hydrogen-generating bacteria are *Clostridium* group bacteria.

4. The method according to claim 3, wherein said organic waste or wastewater is organic waste or wastewater from food processing plants or bioculture plants, agricultural waste, feces and urine, raw sludge, sludge at the bottom of lakes and marshes, or slot sludge.

5. The method according to claim 2, wherein said organic waste or wastewater is organic waste or wastewater from food processing plants or bioculture plants, agricultural waste, feces and urine, raw sludge, sludge at the bottom of lakes and marshes, or slot sludge.

6. The method according to claim 5, wherein the amount of methane that is produced during the culturing step is reduced compared to the amount of methane that is produced from said organic waste or wastewater when said heat-treating step is not conducted.

7. The method according to claim 1, wherein, in Table 1, the treatment time is at least 60 minutes in at least one of A–C, and the treatment time is at least 120 minutes in at least one of D–F.

8. The method according to claim 7, wherein said hydrogen-generating bacteria are *Clostridium* group bacteria.

9. The method according to claim 8, wherein said organic waste or wastewater is organic waste or wastewater from food processing plants or bioculture plants, agricultural waste, feces and urine, raw sludge, sludge at the bottom of lakes and marshes, or slot sludge.

10. The method according to claim 7, wherein said organic waste or wastewater is organic waste or wastewater from food processing plants or bioculture plants, agricultural waste, feces and urine, raw sludge, sludge at the bottom of lakes and marshes, or slot sludge.

11. The method according to claim 7, wherein the amount of methane that is produced during the culturing step is reduced compared to the amount of methane that is produced from said organic waste or wastewater when said heat-treating step is not conducted.

12. The method according to claim 1, wherein said hydrogen-generating bacteria are *Clostridium* group bacteria.

13. The method according to claim 12, wherein said organic waste or wastewater is organic waste or wastewater from food processing plants or bioculture plants, agricultural waste, feces and urine, raw sludge, sludge at the bottom of lakes and marshes, or slot sludge.

14. The method according to claim 12, wherein the amount of methane that is produced during the culturing step is reduced compared to the amount of methane that is produced from said organic waste or wastewater when said heat-treating step is not conducted.

15. The method according to claim 1, wherein said organic waste or wastewater is organic waste or wastewater from food processing plants or bioculture plants, agricultural waste, feces and urine, raw sludge, sludge at the bottom of lakes and marshes, or slot sludge.

16. The method according to claim 15, wherein the amount of methane that is produced during the culturing step is reduced compared to the amount of methane that is produced from said organic waste or wastewater when said heat-treating step is not conducted.

17. The method according to claim 15, wherein, in Table 1, the treatment time is at least 60 minutes in at least one of A–C, and the treatment time is at least 120 minutes in at least one of D–F.

18. The method according to claim 17, wherein said organic waste or wastewater is organic waste or wastewater from food processing plants or bioculture plants, agricultural waste, feces and urine, raw sludge, sludge at the bottom of lakes and marshes, or slot sludge.

19. The method according to claim 17, wherein said hydrogen-generating bacteria are *Clostridium* group bacteria.

20. The method according to claim 1, wherein the amount of methane that is produced during the culturing step is reduced compared to the amount of methane that is produced from said organic waste or wastewater when said heat-treating step is not conducted.

* * * * *